United States Patent [19]

McAuslan

[11] Patent Number: 4,836,884

[45] Date of Patent: Jun. 6, 1989

[54] IMPLANTABLE MATERIALS

[75] Inventor: Brian R. McAuslan, Clareville Beach, Australia

[73] Assignee: Telectronics N.V., Netherlands Antilles

[21] Appl. No.: 113,931

[22] PCT Filed: Feb. 17, 1987

[86] PCT No.: PCT/AU87/00043
§ 371 Date: Dec. 14, 1987
§ 102(e) Date: Dec. 14, 1987

[87] PCT Pub. No.: WO87/05038
PCT Pub. Date: Aug. 27, 1987

[30] Foreign Application Priority Data

Feb. 17, 1986 [AU] Australia .................. PH4637

[51] Int. Cl.[4] .................. B44C 1/22; B29C 37/00
[52] U.S. Cl. .................. 156/629; 156/633; 156/654; 156/668; 252/79.2; 427/2; 427/307; 428/156; 623/66
[58] Field of Search ........... 156/654, 655, 668, 629, 156/630, 633; 252/79.2; 428/156, 170, 411.1; 427/2, 307, 308, 309; 623/1, 2, 3, 4–6, 8, 11, 12, 66

[56] References Cited

U.S. PATENT DOCUMENTS

| | | | |
|---|---|---|---|
| 3,538,521 | 11/1970 | Basner | 5/91 |
| 3,766,650 | 10/1973 | Gnecco | 32/8 |
| 3,826,678 | 7/1974 | Hoffman et al. | 117/81 |
| 4,281,420 | 8/1981 | Raab | 3/1.912 |
| 4,418,162 | 11/1983 | Kasuga et al. | 523/205 |
| 4,451,629 | 5/1984 | Tanaka et al. | 526/238.23 |
| 4,521,273 | 6/1985 | Polek | 156/668 X |
| 4,527,293 | 7/1985 | Eckstein et al. | 623/12 |
| 4,551,417 | 11/1985 | Suzuki et al. | 430/316 |
| 4,648,845 | 3/1987 | Orlowski et al. | 427/2 X |
| 4,655,770 | 4/1987 | Gupta et al. | 623/1 |
| 4,715,858 | 12/1987 | Lindstrom | 427/2 X |

FOREIGN PATENT DOCUMENTS 1131106 9/1982 Canada .
1401233 7/1975 United Kingdom .

Primary Examiner—William A. Powell
Attorney, Agent, or Firm—Gottlieb, Rackman and Reisman

[57] ABSTRACT

Polymer hydrogels are adapted for surgical implants by chemical modification of the surface to stimulate the attachment and growth of cells thereto. The modification may be by oxidative acid etching or by copolymerization with methacrylic acid and diethylaminoethyl methacrylate.

7 Claims, 4 Drawing Sheets

IMPLANTABLE MATERIALS

TECHNICAL FIELD

This invention relates to implantable materials and to processes for their manufacture.

BACKGROUND ART

Blood vessels and naturally occurring internal organs are lined with a thin layer of endothelial cells which have a number of bio-chemical functions. In so far as surgical implants are concerned, one important function of endothelial cells is their involvement in the processes of rendering the surfaces of blood vessels non-thrombogenic.

A key factor in attaining a non-thrombogenic vascular graft is the rapid development of a lining of the endothelial cells on the implant. Thus, such implants benefit from having surfaces that encourage endothelial cell attachment and spreading.

Similar considerations apply in respect of other implants that are intended for prolonged implantation where blood contact is required such as permanent indwelling catheters for drug administration, fluid drainage tubes, vascular shunts, pacemaker leads and implantable transducers.

Synthetic polymer hydrogels have found a wide range of biomedical applications, including controlled drug delivery systems, replacement blood vessels, would dressings, coatings for biosensors, soft tissue substitution and contact lenses.

As a family of polymeric materials, synthetic hydrogels are generally well tolerated when implanted in vivo and can be tailored to suit the many potential functions of prosthetic devices in contact with blood or soft tissues. The success of hydrogels as biomaterials lies partially in their superficial resemblance to living tissue, a property attributable to their relatively high water content (say 20%–99%), which immediately results in minimal frictional irritation of surrounding tissues.

In addition, hydrogels can be non-toxic, chemically stable and (due to their water content) can exhibit a low interfacial tension with aqueous environments. This latter property becomes particularly important in considering the compatibility of blood-contacting surfaces, where minimal interfacial tension has been related to thromboresistance.

The hydrogel polyHEMA—poly(2-hydroxyethyl methacrylate)—is known to possess inherent characteristics of good permeability, water uptake and tolerable polymer/tissue interface disruption which make it a desirable biomaterial (see, for example, Cohn D et al (1984) Radiation—Grafted Polymers for Biomaterial Applications I. 2-Hydroxyethyl Methacrylate: Ethyl Methacrylate Grafting on to Low Density Polyethylene Films *J. App. Pol. Sci.* 29, 2645–2663).

Despite these advantages, however, unmodified polyHEMA does not have the ability to sustain mammalian cell growth and consequently its use as a biomaterial has been restricted to applications where this inability is a positive advantage (see Andrade J. D. (1975) Hydrogels for Medical and Related Applications *ACS SYMPOSIUM SERIES* 31, Washington).

Recent investigations into the effects of treating polystyrene with sulphuric acid (see Curtis A.S.G. et al (1983) Adhesion of Cells to Polystyrene Surfaces *J. Cell Biol* 97, 1500–1506) have shown a marked improvement in the ability of that polymer to support mammalian cell growth after acid etching. Whilst this is not a new concept, modern analytical methods such as electron spectroscopy for chemical analysis have allowed a more detailed study of surface changes occurring with such treatments resulting in some clarification of certain aspects of cell adhesion.

Another disadvantage of polyHEMA is that its poor mechanical properties prevent it from being used as an implant requiring high mechanical strength.

By copolymerisation of polyHEMA with other selected synthetic polymers, it has been possible to manipulate surface charges, hydrophilicity and equilibrium water content to achieve varying degrees of attachment and growth of fibroblastoid cells. An alternative modification has been to incorporate natural polymers such as collagen, elastin and fibronectin in polyHEMA hydrogels. This has provided a model system to study the contribution of such extracellular matrix components to cell adhesion and growth. While this approach has allowed the growth of a wider variety of cell types on such hydrogels, it also places other restrictions and problems on the polyHEMA system as a biomaterial for use in prosthetic devices.

It is an object of this invention to provide an implantable material having improved biocompatibility arriving from enhanced endothelial cell attachment properties.

It is a further object of this invention to provide an improved implantable material having a mechanically acceptable substrate to which is attached a polyHEMA layer.

DISCLOSURE OF THE INVENTION

According to the invention there is provided an implantable material comprising a hydrogel the surface of which is chemically modified so as to stimulate the attachment and growth of cells thereto.

The chemical modification may consist of hydrolytic etching of the hydrogel or copolymerisation of the hydrogel with methacrylic acid.

The surface of a hydrogel of polyHEMA may also be modified by limited surface hydrolysis.

By exposing polyHEMA to a particular acid treatment we have achieved cell attachment and cell growth rates comparable with those of tissue culture polystyrene and better than P.T.F.E (TEFLON), a commonly used biomaterial.

The treated hydrogel of the invention has a surface that supports efficient adhesion of endothelial cells which grow to confluence. Electron spectroscopy chemical analysis of the acid etched polyHEMA indicates an increase in $C=O$ groups relative to $C-O$ groups suggesting that increased negative charge from carboxyl groups contribute to the change in cell-substatum interaction. This contention is supported by the fact that methacrylic acid contributes mainly to increased carboxyl groups in the material.

The cell plating efficiency of an acid etched polyHEMA treated in accordance with the invention increased from 0% to 95% of that of glow-discharge treated polystyrene and fibronectin binding capacity increased from 0 to $2 \times 10^{-11}$ pico mole per square centimeter.

The invention also provides an implantable material consisting of a mechanically acceptable substrate having a hydrogel layer, said hydrogel layer being chemically modified as described above so as to stimulate the attachment and growth of cells thereto.

The substrate may be any convenient material such as polyurethane, TEFLON, DACRON or other plastic material, platinum, titanium or other metal as well as carbon and ceramic materials. The polyHEMA may be attached to the substrate by mechanically keying it to a microporous structure or by grafting in the case of a polymer surface.

According to another aspect of the invention, there is provided a method of providing an implant comprising the steps of:

(a) forming a substrate having pre-determined mechanical properties,
(b) applying a hydrogel layer to the substrate, and,
(c) chemically modifying the surface of the hydrogel so as to stimulate the attachment and growth of cells thereto.

BRIEF DESCRIPTION OF THE DRAWINGS

In order that the invention may be more readily understood and put into practical effect, reference will now be made to the accompanying drawings in which.

BEST MODE FOR CARRYING OUT THE INVENTION

Figure 1:
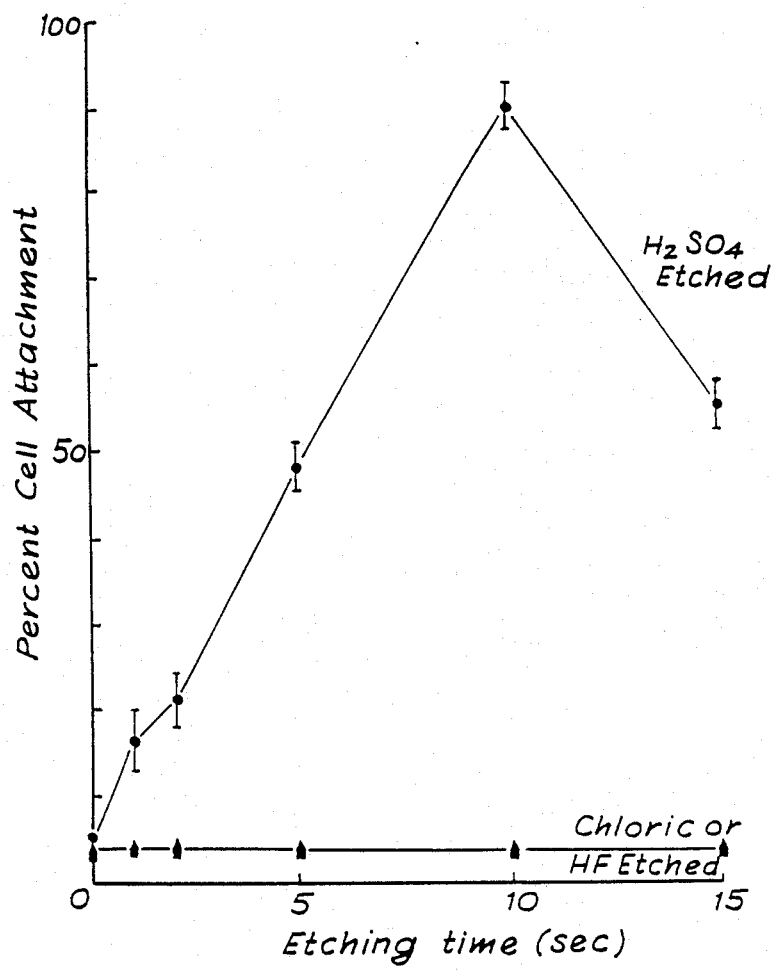
FIG. 1 is a graph of percentage cell attachment as a function of etching time for a polyHEMA substrate etched with sulphuric acid.

The invention will now be described in more detail with reference to the following examples.

EXAMPLE 1

Materials

The material utilised in the examples were:

(i) hydroxyethyl methacrylate (HEMA), Methacrylic Acid (MAA), Diethyl aminoethyl methacrylate (DEAEMA) and Tetraethylene glycol dimethacrylate (TEGDMA).

(ii) [$^{14}$C] Methylated Human fibronectin (specific activity 1.4Ci/mMol) and Bovine Serum Albumin (specific activity 3.5Ci/mMol)

(iii) NCS solubiliser for Liquid scintillation counting.

(iv) Bovine plasma fibronectin (FN) prepared as described in G. N. Hannan, J. W. Redmond, and B. R. McAuslan, "Similarity of the carbohydrate moieties of fibronectins derived from blood plasma and synthesised by cultured endothelial cells," *Biochim. Biophys. Acts*, 801, 396 402 (1984).

(v) Virgin, unfilled P.T.F.E (TEFLON, Registered Trade Mark) sheet, 0.25 mm thick (vi) Segmented polyurethane sheet, 0.2 mm thick was cast from commercially available "Biomer" solution.

Preparation of polymers

PolyHEMA homopolymer was prepared essentially as described by Civerchia-Perez et. al., (L. Civerchia-Perez, B. Faris, G. LaPointe, J. Beldekas, H Leibowitz, and C. Franzblau, "Use of collagen-hydroxyethylmethacrylate hydrogels for cell growth," *Proc. Natl. Acad. Sci. USA*, 77(4), 2064–2068 (1980)) except that the casting of the hydrogels was carried out in a Bio-Rad Slabgel pouring apparatus using 0.75 mm thick Teflon spacers. By varying the thickness of the Teflon spacers gels were successfully cast from 0.25 mm to 1 mm in thickness.

The copolymer hydrogels of polyHEMA/MAA and polyHEMA/DEAEMA were prepared as described by Holly and Refojo (F. J. Holly, and M. F. Refojo, "Wettability of hydrogels I. Poly (2-hydroxyethyl methacrylate)," *J. Biomed. mater. Res.*, 9, 315–326 (1975)), again casting was done in the Bio-Rad apparatus.

After polymerisation, the hydrogels were cut into 14 mm diameter discs and dialysed extensively against phosphate buffered saline pH 7.4.(PBS) It was found that dialysing the membranes prior to cutting into discs was not as efficient with the larger sizes that were able to be cast in the Bio-Rad system. Some swelling of the discs did occur as a result of dialysis but they fitted readily into a 16 mm diameter tissue culture well.

After dialysis the buttons were transferred to PBS containing penicillin, streptomycin and kanamycin and stored at 4° C. Sterilisation by UV for 2 hours was carried out immediately prior to use for cell studies and the sterilised discs equilibrated with an appropriate sterile cell culture medium for one hour. The teflon sheet was cut into 15 mm diameter discs and the polyurethane sheet was cut into squares of 1 cm×1 cm. Both materials were washed extensively with acetone and then absolute ethanol. Sterilisation was achieved by prolonged soaking in absolute ethanol with washes in sterile PBS, or by autoclaving. No detectable differences were obvious from using either method before cell or protein binding assays.

Surface modification of polyHEMA

PolyHEMA homopolymer discs were treated individually as follows.

A disc was placed into a specially constructed polyallomer ladle (2.5 cm in diameter, 2 cm deep with a 6.5 cm×0.75 cm handle, 3 cm diameter perforations were punched out of the bottom of the ladle with a cork borer) and quickly immersed into acid (either sulphuric 98%, hydrochloric, consisting of adding 3 vol. 70% perchloric acid and 2 vol. of saturated aqueous potassium chlorate or hydrofluoric 50%) for predetermined times ranging from 1 to 20 seconds. The perforations in the base of the ladle allowed the acid to act equally on all hydrogel surfaces by creating a turbulent upwelling of acid that suspended the disc in the centre of the ladle. Gentle vertical agitation of the ladle maintained this action. After acid immersion, the ladle and disc were immediately washed in deionised water several times and the disc then transferred to PBS for extensive dialysing. The discs turned opaque in fashion similar to those that were first dialysed after the initial casting of the hydrogel, but quickly cleared. After dialysis the discs were stored and subsequently used in the same manner as described in the hydrogel preparation.

Basic hydrolysis of polyHEMA was carried out at both room temperature and at 78° C. by immersing discs into solutions of 3.0M NaOH for times ranging from 30 minutes to 6 hours. Subsequent washing and dialysis of treated discs was the same as described for the acid treated samples.

Cell culture and cell growth rate determination

A clonal line of normal bovine aortal endothelial cells (BAE) was grown and maintained as previously described.

Single hydrogel discs, Teflon discs and polyurethane squares were placed into separate wells of a Costar cluster dish (24 wells, 16 mm diameter). 1 ml suspensions of $5 \times 10^4$ cells were added to each well and routinely maintained in medium 199 plus 10% fetal calf serum.

To determine cell numbers discs were transferred from wells to 35 mm diameter polystyrene tissue-culture dishes and fixed with 2.5% glutaraldehyde. Counts were obtained for a superimposed grid area representing 0.106 mm$^2$ by using a Bioquant Image Analysis system coupled with an Olympus BH-2 phase contrast microscope. Cell numbers are given as the average and standard deviation of 15 random counts on each of 4 discs, and are expressed per cm$^2$ For translucent materials such as Teflon and polyurethane the cells were stained with Giemsa prior to counting.

Cell attachment determination

Cells were plated onto the various samples as described above and incubated for 6 hrs at 37° C. After incubation the cells were washed with sterile PBS to remove those not attached. Cells on the translucent samples were fixed and stained as described, then all samples counted on the Bioquant System. Cell numbers are given as an average and standard deviation of 15 random counts on each of 4 replicates per sample and expressed as a percentage of equivalent cells attached per cm$^2$ to glow-discharge polystyrene.

EXAMPLE 2

Cell Response to Acid Etched polyHEMA

Bovine Aortal Endothelian (B.A.E.) cells were plated onto a series of polyHEMA substrates that had been exposed to the following sulphuric acid etching treatment times.
(a) nil
(b) 1 second
(c) 2 seconds
(d) 5 seconds
(e) 10 seconds
(f) 15 seconds The percent cell attachment as a function of the sulphuric acid etching time for the polyHEMA substrates is shown in FIG. 1. The percent cell attachment for hydrochloric acid and hydrofluoric acid etched polyHEMA substrates is also shown in FIG. 1 to emphasise the efficacy of the sulphuric acid etch.

EXAMPLE 3

Relative Placing Efficiencies of B.A.E. Cells on Etched polyHEMA v. Teflon

Bovine Aortal Endothelial (B.A.E.) cells were plated onto a sulphuric acid etched polyHEMA substrate and onto a P.T.F.E. (TEFLON) substrate and the number of cells attached after six hours was expressed as a percentage of the number that attached to tissue culture polystyrene The results were:
TEFLON 70-72%
Etched PolyHEMA: 90-95%

The sulphuric acid etched polyHEMA was relatively more efficient in its plating efficiency with respect to tissue culture polystyrene than the P.T.F.E.

EXAMPLE 4

Figure 2:
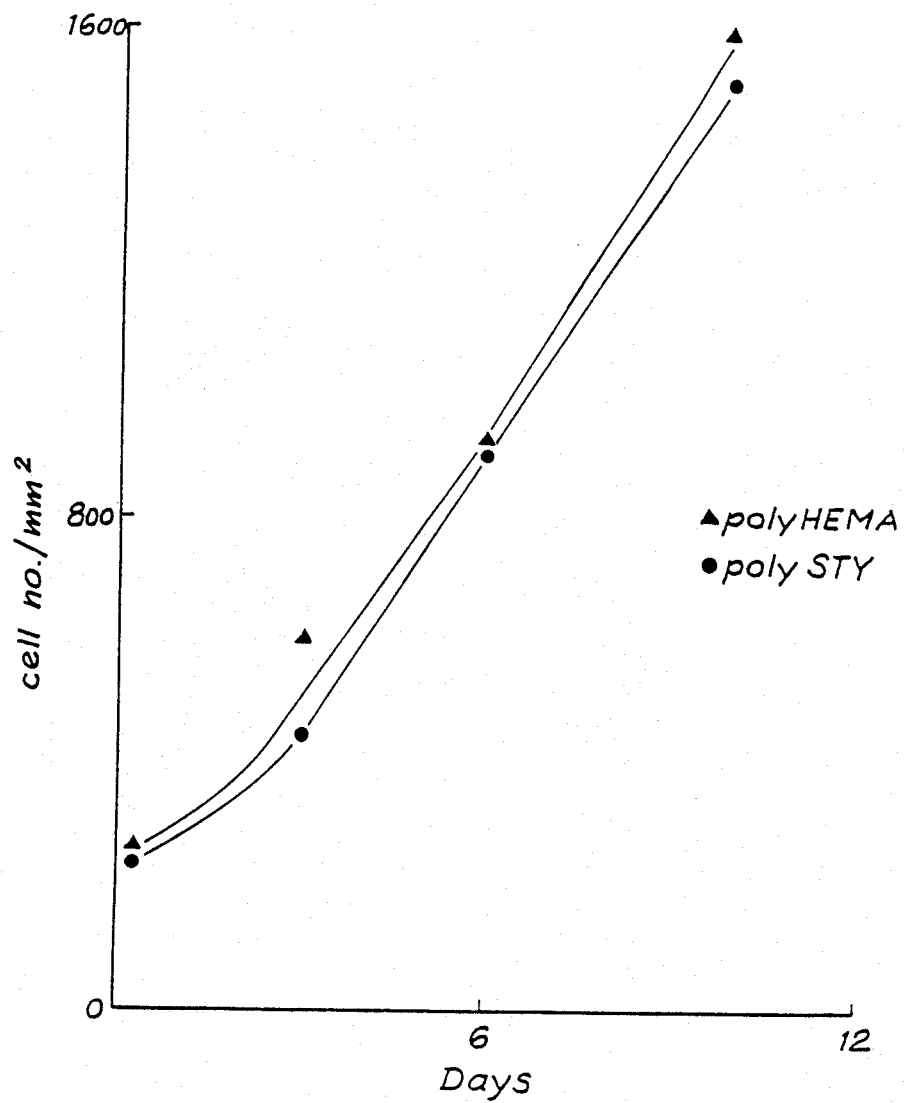
FIG. 2 is a graph of B.A.E. cell growth as a function of time for sulphuric acid etched polyHEMA and glow-discharge treated polystyrene.

Comparative Cell Growth of B.A.E. on Etched polyHEMA and Tissue Culture Polystyrene The growth of B.A.E. cells (number per square millimeter) at 3, 6 and 10 days is shown in FIG. 2 for sulphuric acid etched polyHEMA and glow-discharge treated polystyrene. B.A.E. cell growth to confluence on etched polyHEMA was comparable to that on tissue culture polystyrene both in terms of growth rate and morphology.

EXAMPLE 5

Platelet Binding

Human platelets were prepared from fresh blood and labelled with $^{51}Cr$ (spec. act. 635 uCi/ml) essentially as described by Dacie and Lewis (J. V. Dacie, and S. M. Lewis, *Practical Haematology*, 5th. edn., Churchill Livingstone, Edinburgh (1975). Samples of polymers were mixed with labelled platelets (conc. $5.0 \times 10^8$/ml) and agitated gently for 2 hrs. After mixing the polymers were washed three times with PBS containing 1% BSA then counted. The cell numbers of platelets remaining bound were expressed per cm$^2$ of sample.

Because the application of an endothelial cell binding material to vascular prostheses is ultimately linked to the problem of thrombogenicity, at least a preliminary indication of the thrombogenic potential of a material might be gained from its propensity for platelet binding. From the results obtained (Table III) it is clear that the affinity of platelets for "etched" pHEMA was much greater than for segmented polyurethane or any of the other polymers tested.

EXAMPLE 6

Protein Binding

Materials to be tested were placed individually into Costar cluster dish wells. 0.5 ml of sterile PBS was added to each well, then an appropriate aliquot of either [$^{14}C$] methylated Human fibronectin or [$^{14}C$] methylated bovine serum albumin added to give a final concentration of 0.1 uCi per well. The wells were incubated for 45 mins at 37° C. After incubation the materials were transferred to 20 ml of fresh PBS and washed for one hour, a further rinse in 5 ml of PBS was carried out prior to transferring the materials to liquid scintillation vials. 4 ml of NCS tissue-solubilising solution was added to each vial and then the vials were incubated at 5° C. for 2 hours.

After cooling to room temperature, an appropriate scintillant was added and the samples dark equilibrated at 4° C. overnight prior to counting. The amount of fibronectin and bovine serum albumin bound is the average obtained from 3 buttons per sample and expressed as a percentage of that bound per cm$^2$, to glow-discharge treated polystyrene tissue culture dishes.

Figure 3:
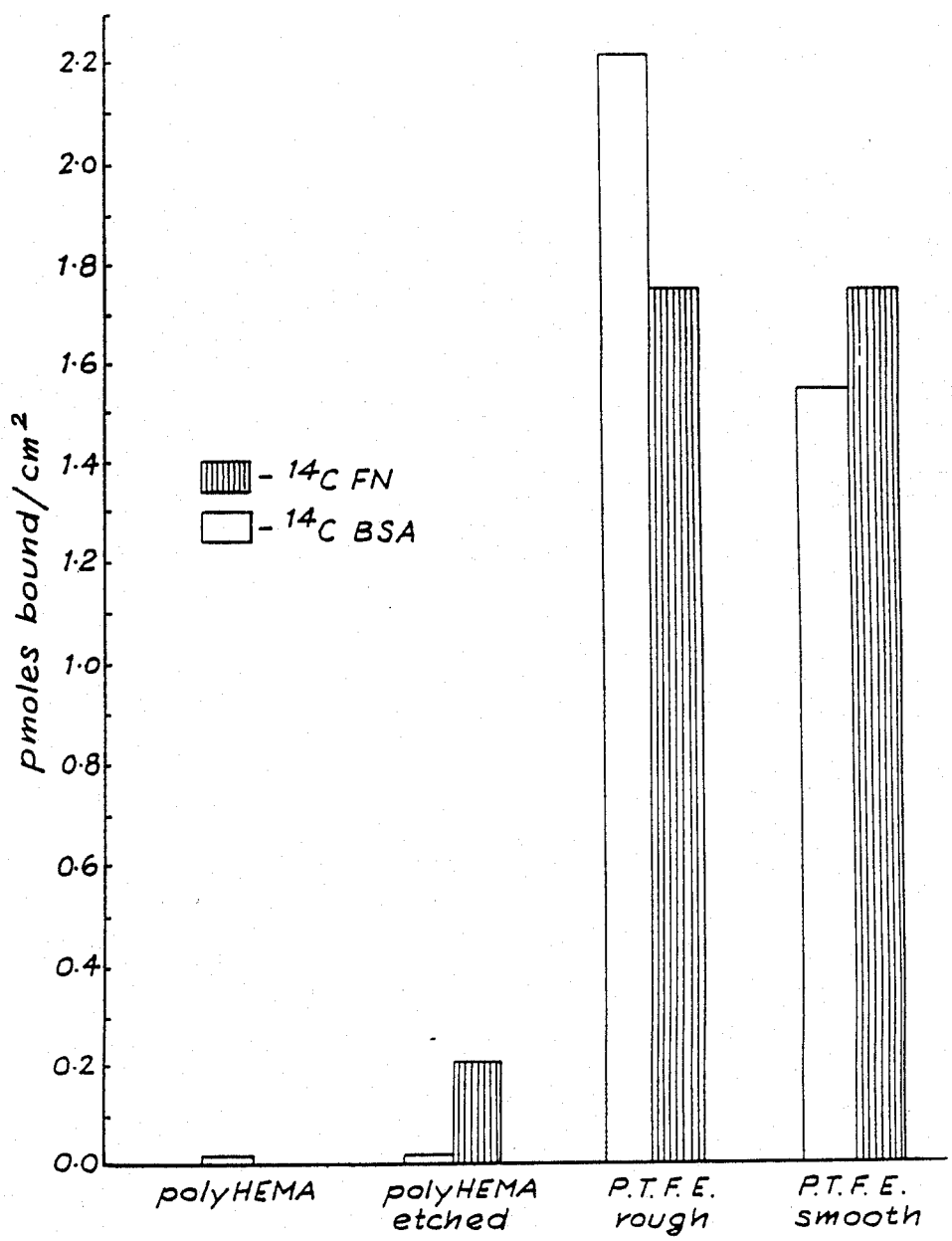
FIG. 3 is a pictorial representation of the protein binding characteristics of etched and non-etched polyHEMA and rough and smooth P.T.F.E., and, FIG. 4 is a graph of percentage cell attachment as a function of percentage copolymer in polyHEMA after copolymerising charged HEMA monomer and with methacrylic acid and diethylaminoethyl methacrylate (DEAEMA).

Initial studies on the propensity of sulphuric acid treated ("etched") polyHEMA to bind blood proteins were conducted with bovine serum albumin and fibronectin. For comparison we used T/C polysty, Teflon and a segmented polyurethane (Biomer). The results are presented in Table II and FIG. 3. PolyHEMA was remarkable in that it showed very weak binding of albumin compared with the other polymers. Acid "etching" did not change this quantitatively. It is known that pHEMA does not bind fibronectin, a major adhesive component of the extracellular matrix. Although acid "etching" did bring about a measurable change, the resultant fibronectin binding capacity was of the order of 10 fold less than for the other polymers studied.

Electron spectroscopy for chemical analysis (ESCA) was used to determine chemical changes in the polymer surfaces. Replicate samples of polyHEMA hydrogel treated with either chloric, hydrofluoric or sulphuric acids were prepared. Samples of each were assayed to ensure their cell adhesive properties were as expected and parallel samples were submitted for ESCA analysis.

For each acid used the most obvious alteration to the polyHEMA surface was indicated by spectral shifts. These changes indicated a significant chemical modification consistent with the creation of surface —COOH groups. Problems raised regarding the correlation of apparent surface changes to biological responses are discussed below.

EXAMPLE 7

Endothelial Cell Attachment to Copolymer Hydrogels

Very little is known about the specific molecular requirements for endothelial cell adhesion in vascular prostheses. The polyHEMA hydrogel with its neutrally charged hydroxyl rich surface is a potentially useful system to explore the requirements for cell attachment, but it has been established that mammalian cells will not adhere to and grow on hydrogels of polyHEMA homopolymer.

To follow the effects of introducing charged groups into the polyHEMA surface a series of hydrogels were prepared from copolymers of HEMA with increasing amounts of methacrylic acid (MAA) or HEMA with increasing amounts of diethylaminoethyl methacrylate (DEAEMA), thus introducing negative carboxyl (—COOH) or positive (amino) charges respectively.

Figure 4:
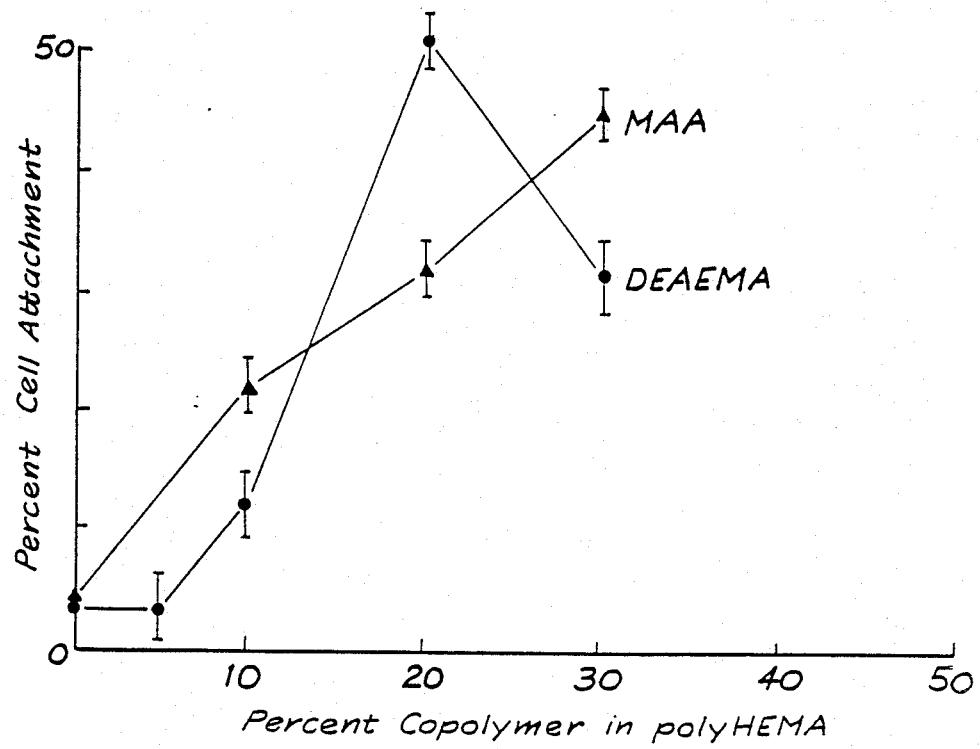

Using endothelial cell attachment (and subsequent growth) as parameters, these copolymers were compared to glow-discharge treated tissue culture grade polystyrene. The attachment capacity of polystyrene for endothelial cells was set at 100% for comparison. When compared with polystyrene the attachment of vascular endothelial cells determined as a plating efficiency, was increased from negligible levels on polyHEMA homopolymer to levels of about 50% after copolymerisation with either MAA or DEAEMA (FIG. 4). Optimal levels were 20% DEAEMA or 30% MAA v/v. Beyond these levels DEAEMA inclusion caused cytotoxic effects leading to cell detachment and arrest of growth.

Methacrylic acid inclusion caused no deleterious effect on cell morphology or growth, but beyond addition to 30% v/v the hydrogel became friable and so physically altered as to be impractical to handle.

The above results discussed in relation to Examples 2 to 7 suggested that either positive or negative charge groups could affect endothelial cell adhesion. The introduction of carboxyl groups was focused on as were other means of introducing such surface charges. The change in properties of polystyrene by acid oxidation is well documented and we tried a similar approach with polyHEMA. PolyHEMA hydrogel buttons were treated with either sulphuric acid hydrofluoric acid or chloric acid. The latter has been shown to be highly effective in creating a cell adhesive surface on polystyrene. The buttons treated for varying times were subsequently washed free of acid then tested for ability to support endothelial cell attachment and growth.

Treatment with either chloric or hydrofluoric acids over a wide range of times caused no demonstrable change in the cell adhesion properties of polyHEMA. In contrast sulphuric acid treatment profoundly altered the surface of the hydrogel such that it became excellent for the adhesion and spreading of vascular endothelial cells (FIG. 1). The morphologic appearance of cells, 24 hours after seeding onto sulphuric acid etched polyHEMA, is shown (FIG. 2) and, provided the optimal etch time (10 sec) was not exceeded, was indistinguishable from those grown on tissue culture grade polystyrene (T/C polysty) The efficiency of attachment of cells to sulphuric acid treated polyHEMA was compared also to Teflon and segmented polyurethane (Table I). The results suggest that etched polyHEMA in this respect was practically as effective as T/C polysty and better than Teflon or polyurethane.

EXAMPLE 8

Endothelial Cell Attachment to Alkali-Treated polyHEMA

In order to determine if cell attachment to surface modified polyHEMA could be induced by non-acid means, several discs were subjected to base hydrolysis. No obvious physical change to the surface of the discs was noted in any of the treatments with 3.0M NaOH at room temperature. Those discs subjected to increasing times in 3.0M NaOH at 78° C., however, showed signs of surface cracking after 6 hours (that was similar to a 15 second treatment with sulphuric acid). Subsequent testing of all the alkali treated discs failed to reveal any changes in the ability of the hydrogel to support cell attachment and growth.

EXAMPLE 9

Cell Growth Rate on Acid-Treaded polyHEMA

Sulphuric acid-treated polyHEMA hydrogel was compared to T/C polystyrene for their ability to support growth of aortal endothelial cells (BAE). No significant difference between them was found in respect to rate of cell growth and final cell density achieved.

The failure of polyHEMA to support adherence of mammalian cells is well documented. A contrary report often cited in reference to cell growth control has been dismissed as an artefact of discontinuous cell-substratum interactions. The results show that brief exposure of a polyHEMA hydrogel surface to concentrated sulphuric acid results in a substratum to which vascular endothelial cells attach and grow virtually as well as they do on the best available tissue culture grade of glow-discharge treated polystyrene. Preliminary results indicate that a polyHEMA. The "etched" polyHEMA surface gave a more uniform attachment and subsequent growth of endothelial cells than did Teflon and this may be advantageous where preliminary endothelial cell seeding can be employed and where uniform surface repopulation is desirable.

Early work on polystyrene "etching" first centred on sulphonic groups for cell attachment. This idea was subsequently discounted and later studies concluded that introduction of —OH groups rather than —COOH groups were essential for mammalian cell attachment. This does not appear likely in the polyHEMA system where it is initially an hydroxyl rich surface that is rendered adhesive following the introduction of —COOH groups.

ESCA analysis of the sulphuric acid treated polyHEMA indicated that the major change was due to creation of —COOH groups which would have resulted in an increase in negative charges on the hydrogel surface. This was confirmed by observations on a corresponding increase in the affinity for cationic dyes (e.g. Crystal Violet, Acridine Orange). This analysis also correlates with the enhanced cell attachment property introduced by copolymerisation with methacrylic acid.

Preliminary evidence suggests that glycol was a by-product of the "etching" procedure. Thus we propose that a likely effect of brief sulphuric acid "etching" is to enhance cell interaction by a limited hydrolysis of polyHEMA to produce polymethacrylic acid as shown:

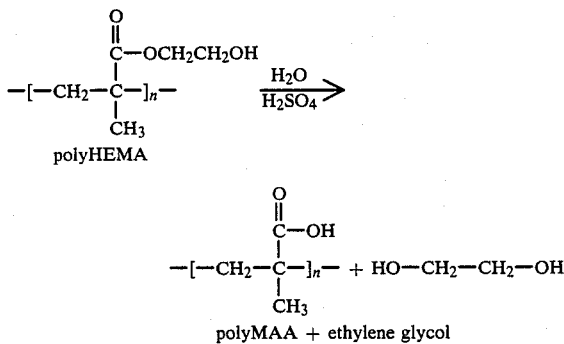

polyMAA + ethylene glycol

Methacrylic acid groups on the hydrogel surface may also sufficiently alter the degree of hydration to promote cell attachment.

Hydrochloric or hydrofluoric acid "etching" lead to reformation of surface carboxyl groups and surfaces which presented similar spectra to that elicited by sulphuric acid "etching". However, hydrochloric or hydrofluoric treatment consistently failed to change the adhesive characteristics of polyHEMA for cells. The hydrolytic treatment of polyHEMA under alkaline conditions, however, demonstrates that simple hydrolysis by acid or basic means elicits changes that do not necessarily lead to conditions suitable for cell attachment. Conceivably higher cross-linking or specific—COOH orientation may occur with those treatments that fail to produce such surface modification.

It is conceivable that attachment of cells to "etched" polyHEMA is mediated by a serum protein such as fibronectin The small but significant increase in ability of polyHEMA to bind fibronectin following acid "etching" is not inconsistent with this idea. However hydrochloric acid or hydrofluoric acid "etching" hydrogels bound fibronectin just as efficiently (Table II) but these did not support cell attachment. Therefore it is unlikely that cell attachment to sulphuric "etched" polyHEMA is simply a result of its ability to bind fibronectin.

Various modifications may be made in details of composition and of the process without departing from the scope and ambit of the invention.

TABLE I

| Polymer | Cell Attachment (6 hr) % per cm$^2$* |
|---|---|
| T/C polysty | 100 |

TABLE I-continued

| Polymer | Cell Attachment (6 hr) % per cm$^2$* |
|---|---|
| Etched polyHEMA | 90 |
| Teflon | 75 |
| Polyurethane | 73 |
| polyHEMA | 1 |

*T/C polysty set as maximal attachment.

Relative attachment of BAE cells to various polymers. Numbers attached were expressed as a percentage of the number of cells attaching to T/C polysty.

TABLE II

| | FN and BSA Binding | | | |
|---|---|---|---|---|
| | FN | | BSA | |
| | pmol · cm$^2$ | % | pmol · cm$^2$ | % |
| polysty | 1.31 | 100 | 1.20 | 100 |
| polyHEMA | 0 | 0 | 0.03 | 2.5 |
| etched polyHEMA (H$_2$SO$_4$) | 0.21 | 16.0 | 0.03 | 2.5 |
| etched polyHEMA (Chloric) | 0.14 | 10.7 | 0.02 | 1.7 |
| Teflon (P.T.F.E.) | 1.74 | 132.8 | 1.88 | 156.7 |
| polyurethane (Biomer) | 1.34 | 102.3 | 2.03 | 169.2 |

Binding of fibronectin (FN) and bovine serum albumin (BSA) to polymers.

TABLE III

| | Relative Platelet Binding |
|---|---|
| Polymer | No. Platelets Bound/cm$^2$ |
| polyHEMA | $1.0 \times 10^5$ |
| polyHEMA etched | $2.0 \times 10^6$ |
| P.T.F.E. (Teflon) | $6.8 \times 10^5$ |
| polyurethane (biomor) | $6.5 \times 10^5$ |

Human platelets prepared from fresh blood were labelled with $^{51}$Cr. Labelled platelets were incubated with polymer samples and number of platelets bound per cm$^2$ in 12 hours from the known specific activity of the inoculum and the radioactivity bound to samples.

I claim:

1. An implantable material comprising a substrate having a surface and a polyHEMA hydrogel applied to said surface which is chemically modified by means of hydrolytic etching by an acid in order to alter the condition of said surface form a non-adhesive state to an adhesive state and thereby promote the attachment and growth of cells to said surface.

2. An implantable material according to claim 1 wherein the hydrogel is a synthetic hydrogel.

3. An implantable material according to claim 1 wherein said acid is sulphuric acid of strength 36N (98%).

4. An implantable material according to claim 1 wherein said hydrolytic etching is carried out for a period of less than 15 seconds.

5. A method of forming an implantable material comprising the steps of:
   (a) forming a substrate having a surface,
   (b) applying a polyHEMA hydrogel layer to the surface of the substrate, and
   (c) chemically modifying the polyHEMA hydrogel by means of hydrolytic etching by an acid in order to alter the condition of said surface from a non-adhesive state to an adhesive state and thereby promote the attachment and growth of cells to said surface.

6. A method according to claim 5 where hydrolytic etching by an acid utilizes sulphuric acid of a strength 36N (98%).

7. A method according to claim 6 wherein said acid etching is performed for a period of less than 15 seconds.

* * * * *